(12) United States Patent
Lariviere et al.

(10) Patent No.: US 6,494,871 B1
(45) Date of Patent: Dec. 17, 2002

(54) SANITARY ABSORBENT NAPKIN

(75) Inventors: Christiane Lariviere; Roya Mohmad, both of Montreal; Zulfikar Murji, Verdun; Sylvain Mongeau, Mascouche, all of (CA)

(73) Assignee: Johnson & Johnson Inc., Montreal (CA)

(\*) Notice: Subject to any disclaimer, the term of this patent is extended or adjusted under 35 U.S.C. 154(b) by 15 days.

(21) Appl. No.: 09/708,262

(22) Filed: Nov. 8, 2000

(51) Int. Cl.[7] .................................................. A61F 13/15
(52) U.S. Cl. .............................. 604/385.23; 604/385.01
(58) Field of Search ........................ 604/385.23, 385.01

(56) References Cited

U.S. PATENT DOCUMENTS

| 4,518,451 A | 5/1985 | Luceri et al. |
|---|---|---|
| 4,555,430 A | 11/1985 | Mays |
| 4,690,679 A | 9/1987 | Mattingly et al. |
| 5,069,676 A | 12/1991 | Ito et al. |
| 5,575,786 A | 11/1996 | Osborne, III |
| 5,607,414 A | 3/1997 | Richards et al. |
| 5,643,240 A | \* 7/1997 | Jackson et al. ............. 604/378 |
| 5,728,083 A | \* 3/1998 | Cohen et al. ............... 604/368 |
| 5,866,242 A | 2/1999 | Tan et al. |
| 6,131,254 A | \* 10/2000 | Cole et al. ..................... 28/121 |

FOREIGN PATENT DOCUMENTS

| DE | 29703589 U1 | 7/1997 |
|---|---|---|
| EP | 0 293 208 A1 | 11/1988 |
| EP | 0 305 970 A2 | 3/1989 |
| EP | 0 804 916 A1 | 11/1997 |
| EP | 0 852 938 A2 | 7/1998 |
| RO | 111726 | 1/2000 |
| WO | WO 98/51250 A1 | 11/1998 |

\* cited by examiner

*Primary Examiner*—Andy Falik
(74) *Attorney, Agent, or Firm*—James P. Barr

(57) ABSTRACT

A sanitary absorbent napkin has a laminate structure coprising a first liquid-permeable sheet of material, a second liquid-permeable sheet of material disposed adjacent the first sheet, and an absorbent member for absorbing liquid and disposed adjacent to the second sheet. The second sheet is arranged to receive the liquid deposited on the first sheet and to transfer liquid to the absorbent member. The napkin has a thickness of less than or equal to about 5 mm, when dry, and a penetration time of less than 15 seconds.

37 Claims, 4 Drawing Sheets

SANITARY ABSORBENT NAPKIN

FIELD OF THE INVENTION

The present invention relates generally to sanitary absorbent articles and in particular to feminine sanitary absorbent napkins which are thin, yet highly absorbent.

BACKGROUND OF THE INVENTION

Externally worn, sanitary absorbent napkins are one of the many kinds of feminine protection devices currently available. The development of materials having a high liquid absorption capacity per unit volume has allowed the required overall thickness of sanitary napkins to be reduced, thereby providing a product which is more comfortable and less obtrusive to wear. Thin sanitary napkins are generally constructed of multiple layers of material each having a particular function, as for example disclosed in U.S. Pat. No. 5,575,786 to T. W. Osborne III. The sanitary napkin disclosed in this document includes a top sheet, an acquisition or transfer sheet, an absorbent core and a barrier sheet. The top sheet serves as the initial layer onto which liquid is first deposited and comprises a material which is pervious but non-absorbent to liquids, to provide a contact surface with the wearer which remains dry. The acquisition sheet which lies between the top sheet and the absorbent core acts to spread liquid from a localized position on the top sheet over a wider area so that liquid is presented to the absorbent core over a relatively large proportion of its surface area. Thus, the acquisition layer is made from a material which has good lateral wicking characteristics. The acquisition layer also serves as an intermediate buffer, providing initial absorption and temporary retention of liquid to allow time for the liquid to be drawn into the absorbent core after its initial deposition on the top sheet.

The absorbent core serves as the main reservoir for liquid deposited on the sanitary napkin and therefore has a high liquid absorption capacity. Materials used for the absorbent core include wood pulp, creped cellulose wadding, absorbent foams and sponges, polymeric fibers and polymeric gelling agents. The material should also be capable of retaining liquid under pressure to prevent rewetting of the acquisition layer and top sheet.

The barrier sheet is made from a material which is impervious to liquid absorbed into the absorbent core and serves as a protective barrier between the absorbent core material and the wearers clothing.

In the above construction, the acquisition or transfer layer is designed to promote lateral irrigation of liquid so that the absorbent core is effective in rapidly and efficiently drawing liquid away from the acquisition layer. However, a drawback of this known construction is that liquid can be drawn all the way to the edge of the acquisition layer and wet the top sheet resulting in undesirable leakage of liquid from the napkin, discomfort to the wearer and staining of the wearer's garments.

Therefore, there is a need for a thin sanitary absorbent napkin which reduces the risk of leakage.

According to the present invention there is provided a sanitary napkin adapted to be worn in the crotch portion of an undergarment comprising: a first liquid-permeable sheet of material, a second liquid-permeable sheet of material disposed adjacent the first sheet, an absorbent member for absorbing liquid and disposed adjacent the second sheet, said second sheet being arranged to receive liquid deposited on said first sheet and to transfer the liquid to said absorbent member, wherein said napkin has a thickness of less than or equal to about 5 mm, when dry, and a penetration time of less than 15 seconds.

The "penetration time" is defined as the time taken for the napkin to absorb a predetermined quantity of a specific liquid in accordance with the test procedure described in detail below. The inventors have found that a construction which gives a penetration time of less than 15 seconds prevents dispersion of liquid to the edges of the transfer layer thereby virtually eliminating the risk of leakage through the edge of the top sheet. In contrast, it has been found that known, thin sanitary absorbent napkins, which have a tendency to leak through the above mechanism, have penetration times of about 25 seconds.

Preferably, the first liquid permeable sheet has an open pore structure and little absorption capacity to allow liquid to be drawn rapidly away from the upper, body-facing surface into the adjacent second liquid-permeable sheet.

In a preferred embodiment, the second liquid-permeable sheet comprises a material having a structure with relatively open pores for efficiently absorbing liquid from the first sheet. The second sheet may comprise a material having a density in the range from about 0.04 to 0.05 g/cc, a basis weight of between about 80 and 110 g/m$^2$ and a thickness in the range of about 2 to 3 mm.

In a preferred embodiment, the napkin has at least one and preferably a plurality of spaced-apart, elongate channel formations arranged to direct liquid therealong for subsequent absorption into the second sheet. The channel(s) extend generally in the plane of the napkin, i.e. laterally, e.g. generally parallel to the surface of the first and/or second sheets. The channels may be formed in the first and/or second sheets and/or between the two. The channel(s) may extend obliquely to the longitudinal axis and may be linear or arcuate. The inventors have found that the provision of channels has an effect on reducing the penetration time as defined by the test procedure described hereinbelow. Advantageously, the channel(s) may be formed by applying pressure to localized regions of the napkin, for example by embossing, which has the simultaneous effect of densifying the material at the floor of the channel, enabling liquid to flow further along the channel before being absorbed. Advantageously, the second sheet may include fusible fibers such as thermoplastic fibers. It has been found that thermoplastic fibers conveniently assist in providing the requisite combination of liquid permeability and wicking properties and at the same time assist in the formation of the channels by embossing and in preserving the shape of the channels over time.

In a preferred embodiment, the absorbent member includes superabsorbent material and may include a mixture of cellulosic fibers and superabsorbent material.

Preferably, the absorbent member comprises an absorbent material having a basis weight of from about 100 g/m$^2$ to about 700 g/m$^2$ which has been air-laid as a bottom layer of pulp, a middle layer of pulp and superabsorbent polymer disposed in amongst the pulp, and a top layer containing at least some pulp.

In a preferred embodiment, the absorbent member has a density of more than about 0.25 g/cc, and more preferably from about 0.3 to 0.4 g/cc.

Preferably, the absorbent member includes from about 5 weight percent to about 60 weight percent superabsorbent polymer, and more preferably in the range of about 30 to 40 weight percent superabsorbent polymer.

In a preferred embodiment, the absorbent material has a basis weight in the range from about 150 g/m$^2$ to about 350 g/m² and more preferably in the range from about 200 g/m² to about 300 g/m².

BRIEF DESCRIPTION OF THE DRAWINGS

Examples of embodiments of the present invention will now be described with reference to the drawings, in which.

DESCRIPTION OF THE PREFERRED EMBODIMENTS

Figure 1:
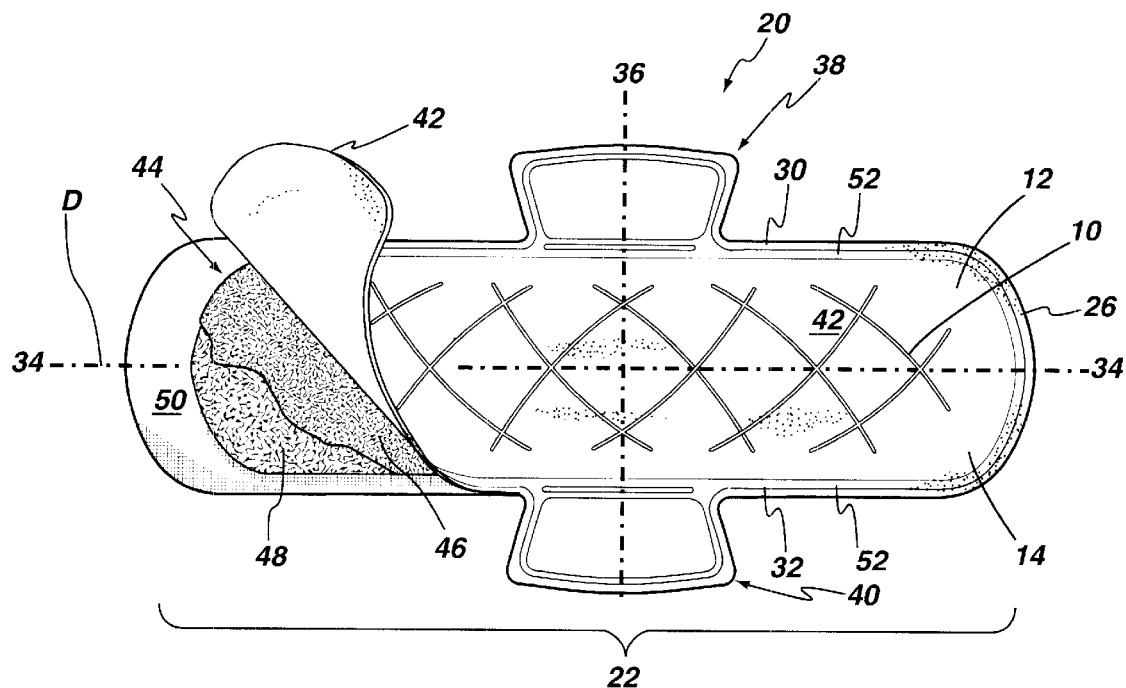
FIG. 1 is a top elevational view of a sanitary napkin in accordance with an embodiment of the present invention, the cover layer of the sanitary napkin being partly removed to show the absorbent system.
Figure 2:
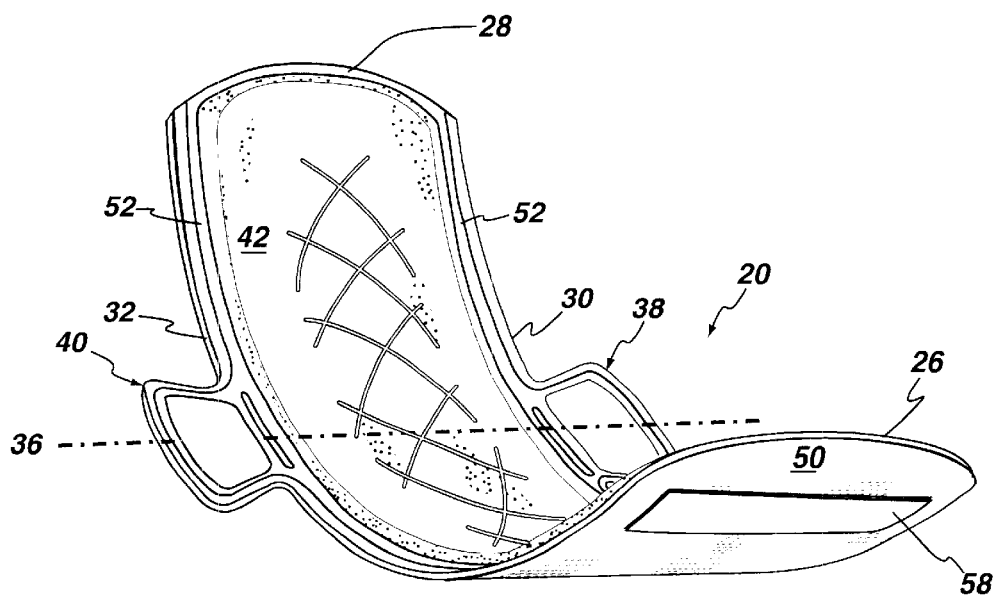
FIG. 2 is a perspective view of the sanitary napkin of FIG. 1, depicted in a position attained when the sanitary napkin is placed in the undergarment of a wearer.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. Each of these sides is arcuate. The main body also has two longitudinal sides, namely a longitudinal side 30 and a longitudinal side 32. The sanitary napkin 20 has a thickness not exceeding about 5 mm. Preferably, the thickness is less than 3.5 mm, more preferably less than 3 mm, and most preferably, it is of about 2.8 mm.

The sanitary napkin 20 has a longitudinal centerline 34 that is an imaginary line bisecting the sanitary napkin 20 in two identical halves.

Projecting laterally outward from each of the longitudinal sides 30, 32 is a flap 38, 40 (respectively). The flaps 38, 40 are in the shape of an isosceles trapezoid with the top adjoining the longitudinal side and the base at the distal end. The main body 22 also has an imaginary transverse centerline 36 perpendicular to the longitudinal centerline 34 and simultaneously bisecting the flaps 38, 40.

Figure 4:
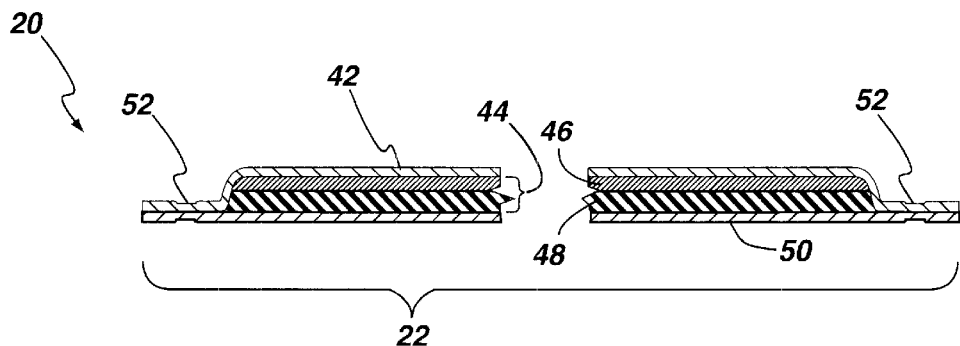
FIG. 4 is a cross-sectional view taken along the longitudinal center line of the sanitary napkin shown in FIG. 3.

As depicted in FIG. 4, the main body 22 is of a laminate construction and preferably comprises a fluid-permeable cover layer 42, an absorbent system 44, and a fluid-impervious barrier layer 50. The absorbent system has preferably two components, namely a first absorbent layer 46 (commonly known as "transfer layer") and a second absorbent layer 48 (commonly known as "absorbent core"). Alternatively, a single layer, namely the second absorbent layer 48, can form the absorbent system 44. Each of these layers is described in hereinbelow.

Main Body—Cover Layer

The cover layer 42 may be a relatively low density, bulky, high-loft non-woven web material. The cover layer 42 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. An example is the non-woven cover layer of sanitary napkins sold by Johnson & Johnson Inc. of Montreal, Canada under the trademark Stayfree Ultra-Thin Cottony Dry Cover.

Bi-component fibers may be made up of a polyester layer and a an polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the adjacent first absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Therefore, the cover layer contributes little to the time taken for the napkin to absorb a given quantity of liquid (penetration time). Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

Alternatively, the cover layer 42 can also be made of polymer film having large pores. Because of such high porosity, the film accomplishes the function of quickly transferring body fluid to the inner layers of the absorbent system. Apertured co-extruded films such described in U.S. Pat. No. 4,690,679 and available on sanitary napkins sold by Johnson & Johnson Inc. of Montreal, Canada could be useful as cover layers in the present invention.

The cover layer 42 may be embossed to the remainder of the absorbent system 44 in order to aid in promoting hydrophilicity by fusing the cover to the next layer. Such fusion may be effected locally, at a plurality of sites or over the entire contact surface of cover layer 42 absorbent system 44. Alternatively, the cover layer 42 may be attached to the absorbent system 44 by other means such as by adhesion.

Main Body—Absorbent System—First Absorbent Layer

Adjacent to the cover layer 42 on its inner side and bonded to the cover layer 42 is a first absorbent layer 46 that forms part of the absorbent system 44. The first absorbent layer 46 provides the means of receiving body fluid from the cover layer 42 and holding it until an underlying second absorbent layer has an opportunity to absorb the fluid, and therefore serves as a fluid transfer or acquisition layer.

The first absorbent layer 46 is, preferably, more dense and has a larger proportion of smaller pores than the cover layer 42. These attributes allow the first absorbent layer 46 to contain body fluid and hold it away from the outer side of the cover layer 42, thereby preventing the fluid from re-wetting the cover layer 42 and its surface. However, the first absorbent layer 46 is not so dense as to prevent the passage of the fluid through the layer 46 into the underlying second absorbent layer 48.

The first absorbent layer 46 may be composed of fibrous materials, such as wood pulp, polyester, rayon, flexible foam, or the like, or combinations thereof. The first absorbent layer 46 may also comprise thermoplastic fibers for the purpose of stabilizing the layer and maintaining its structural integrity. The first absorbent layer 46 may be treated with surfactant on one or both sides in order to increase its wettability, although generally the first absorbent layer 46 is relatively hydrophilic and may not require treatment. The first absorbent layer 46 is preferably bonded on both sides to the adjacent layers, i.e. the cover layer 42 and an underlying second absorbent layer 48.

Materials particularly suitable for use in the first absorbent layer 46 which the inventors have found contribute to reducing the penetration time have a density in the range of about 0.04 to 0.05 g/cc, a basis weight in the range from about 80 to 110 g/m$^2$ and a thickness in the range of about 2 to 3 mm and in particular, a thickness of 2.6 mm. Examples of materials suitable for the first absorbent layer are through air bonded pulp sold by BUCKEYE of Memphis, Tenn. under the designation VIZORB 3008, which has a basis weight of 110 g/m$^2$ and VIZORB 3010, which has a basis weight of 90 g/m$^2$.

Main Body—Absorbent System—Second Absorbent Layer

Immediately adjacent to and bonded to the first absorbent layer 46 is the second absorbent layer 48.

In one embodiment, the first absorbent layer 46 has a central width that is at least about the same as the central width of the second absorbent layer 48. In a specific embodiment, this central width is greater than about 64 mm. In another embodiment, the first absorbent layer 46 has a central width that exceeds the central width of the second absorbent layer 48. The term "central width" refers to a specific area of a layer, such as an absorbent layer determinable as follows. A reference point on the sample layer that is disposed beneath the center of the vaginal orifice, when worn, is located. A plane parallel to the transverse centerline 36 and 3.75 centimeters forward from the reference point in the direction of the wearer's mons pubis is located. Another plane parallel to the lateral centerline 36 and 5.0 centimeters rearward from the reference point in the direction of the wearer's buttocks is also located. The greatest flat-out, uncompressed, unmanipulated, lateral width of the sample layer between the two planes is the absorbent width of the sample layer.

The central width of the absorbent system, when the absorbent system includes a plurality of absorbent layers is the central width of the layer of the absorbent system that has the largest central width. In a specific example, the central width of the absorbent system exceeds 64 mm.

In one embodiment, the second absorbent layer 48 is a blend or mixture of cellulosic fibers and superabsorbent disposed in and amongst fibers of that pulp.

In a specific example, the second absorbent layer 48 is a material containing from about 40 weight percent to about 90 weight percent cellulosic fibers; and from about 5 weight percent to about 60 weight percent SAP (superabsorbent polymers). The material has a water content of less than about 10 weight percent. As used herein, the phrase "weight percent" means weight of substance per weight of final material. By way of example, 10 weight percent SAP means 10 g/m$^2$ SAP per 100 g/m$^2$ basis weight of the material.

Cellulosic fibers that can be used in the second absorbent layer 48 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The second absorbent layer 48 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, and the product offered by Chemdal International, Inc. of Palatine, Ill., under the designation of 2100A*.

In a specific example, the second absorbent layer 48 is a material containing from about 50 to about 90 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

Figure 5:
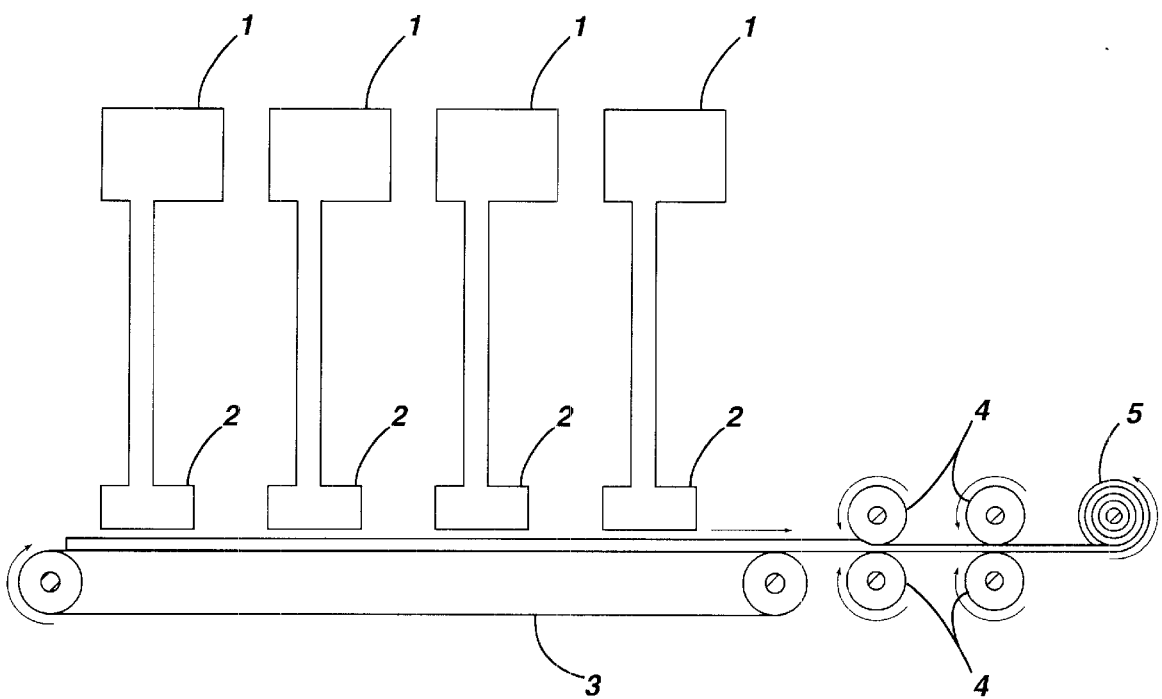
FIG. 5 is a schematic illustration of means for air-laying absorbent material for making an example of an absorbent core of the sanitary napkin according to an embodiment of the present invention, using four air-laying heads followed by means for compacting the air-layered material.

The second absorbent layer 48 can be manufactured by using air-laying means well known in the art (See FIG. 5). In accordance with FIG. 5, cellulosic fibers (e.g., pulp) are processed using a hammer mill to individualize the fibers. The individualized fibers are blended with SAP granules in a blending system I and pneumatically conveyed into a series of forming heads 2. The blending and distribution of fibers and SAP granules can be controlled separately for each forming head. Controlled air circulation and winged agitators in each chamber produce uniform mixture and distribution of pulp and SAP. The SAP can be thoroughly and homogeneously blended throughout the material or contained only in specific strata by distributing it to selected forming heads. Fibers (and SAP) from each forming chamber are deposited by vacuum onto a forming wire 3 thus forming a layered absorbent web. The web is subsequently compressed using calenders 4 to achieve desirable density. The densified web is wound into a roll 5 using conventional winding equipment. The forming wire 3 can be covered with tissue paper to reduce the loss of material. The tissue paper layer can be removed prior to calendering or incorporated into the formed material. In a possible variant, the first absorbent layer 46 can be formed integrally with the second absorbent layer 48 to provide a unitized absorbent system 44. This can be achieved by providing the apparatus depicted in FIG. 5 with an additional forming head (not shown in the drawings) to deposit on the second absorbent layer 48, by air laying and prior to calendering, a layer of material to form the first absorbent layer 46.

The second absorbent layer 48 of the present invention is of high density and in a specific example has a density of greater than about 0.25 is g/cc. Specifically, the second absorbent layer 48 may have a density in the range of from about 0.30 g/cc to about 0.50 g/cc. More specifically, the density is from about 0.30 g/cc to about 0.45 g/cc and, even more specifically from about 0.30 g/cc to about 0.40 g/cc.

Air-laid absorbents are typically produced with a low density. To achieve higher density levels, such as the examples of the second absorbent layer 48 given above, the air-laid material is compacted using calenders as shown in FIG. 5. Compaction is accomplished using means well known in the art. Typically such compaction is carried out at a temperature of about 100 degrees C and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved.

In one embodiment the second absorbent layer 48 has a ratio of Gurley stiffness, measured in milligrams (mg) to density, measured in grams per cubic centimeter (g/cc), of less than about 3700. In a specific example, that ratio of Gurley stiffness to density is less than about 3200 and, more specifically, less than about 3000.

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171 E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams.

The second absorbent layer 48 is strong in light of its softness. Pad integrity is a well-known measurement of absorbent material strength. In a specific embodiment the second absorbent layer 48 demonstrates strength (high pad integrity) over a wide range of densities. In a specific example the second absorbent layer 48 has a pad integrity, measured in Newtons (N), to density (g/cc) ratio of greater than about 25.0. In a more specific example, that ratio is greater than about 30.0 and, could even be greater than about 35.0. The pad integrity is a test performed on an Instron Universal Testing Machine. Essentially, the test measures the load required to pierce through the test sample, as described in the PFI Method of 1981. A test sample having dimensions of 50 mm by 50 mm is clamped on the Instron with a suitable fastening device. A 20 mm diameter piston traveling at the rate of 50 mm/min punctures the stationary sample. The force required to puncture the sample is measured in Newtons (N).

The second absorbent layer 48 can be prepared over a wide range of basis weights. The second absorbent layer 48 can have a basis weight in the range of from about 100 g/m$^2$ to about 700 g/m$^2$. In a specific example, the basis weight ranges from about 150 g/m$^2$ to about 350 g/m$^2$. Preferably the basis weight ranges from about 200 g/m$^2$ to about 300 g/m$^2$ and, more preferably, to about 250 g/m$^2$.

The second absorbent layer 48 functions synergistically with the first absorbent layer to reduce the penetration time. The first absorbent layer, having a relatively open structure, allows liquid to pass relatively easily to the second absorbent layer, which has a high cappiliarity and therefore strength in pulling liquid from the first absorbent layer into its bulk. In a specific embodiment, the second absorbent layer contains 30 to 40 percent weight superabsorbent material such as superabsorbent polymer, has a basis weight in the range of about 200 to 300 g/m$^2$ and a density in the range from about 0.2 to 0.4 g/cc.

The second absorbent layer 48 can be formed as a three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

An interesting characteristic of the second absorbent layer 48 is its ability to retain SAP when subjected to mechanical stress. The second absorbent layer 48 retained over 85 percent by weight of its SAP content when subjected to 10 minutes of rigorous shaking. Specifically, a material of this invention retains over 90 percent, more specifically over 95 percent and, even more specifically over 99 percent of its SAP under these mechanical stresses. The percent of SAP retained was determined by shaking the material in a Ro-Tap Sieve Shaker manufactured by W. S. Tyler Co., Cleveland Ohio. More specifically the sample is placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the sample, "free SAP", was determined by combining the residue contained in each of the sieves and separating the cellulosic fiber from the SAP.

Even where prepared as from multiple layers, the final thickness of the formed second absorbent layer 48 is low. The thickness can vary from about 0.5 mm to about 2.5 mm. In a specific example, the thickness is from about 1.0 mm to about 2.0 mm and, even more specifically from about 1.25 to about 1.75 mm.

Figure 6A:
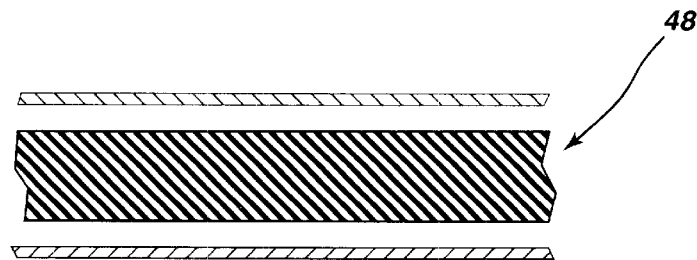
FIG. 6 shows three and four layer embodiments of an absorbent core that can be used in the sanitary napkin of an embodiment of the invention.
Figure 6B:
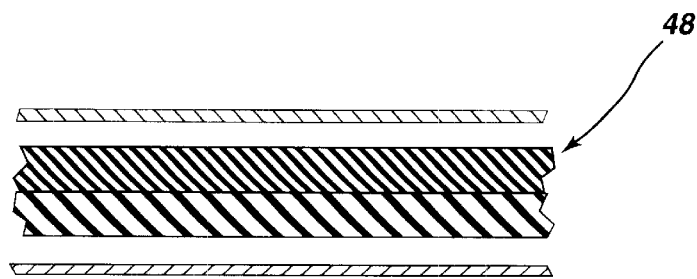

One embodiment of the second absorbent layer 48 particularly well suited for use in the sanitary napkin 20 is depicted in FIG. 6. Such second absorbent layer 48 has a basis weight of from about 200 g/m$^2$ to about 350 g/m$^2$ and a density between about 0.3 g/cc and 0.5 g/cc. In a specific example, the density is from about 0.3 g/cc to about 0.45 g/cc and, more specifically about 0.4 g/cc.

The second absorbent layer 48 depicted in FIG. 6 is air-laid as three strata: a bottom layer of pulp (without superabsorbent) with a basis weight of about 25 g/m$^2$; a middle layer with a basis weight of about 150 g/m$^2$ and which contains from about 10 to about 30 g/m$^2$ superabsorbent and from about 120 g/m$^2$ to about 140 g/m$^2$ pulp; and a top layer of pulp (without superabsorbent) with a basis weight of about 25 g/m$^2$. Relative to the total basis weight of the second absorbent layer 48, the level of superabsorbent ranges from about 5 to about 15 weight percent (g/m$^2$ of superabsorbent per g/m$^2$ material). In a specific example, the level of superabsorbent is from about 7.5 weight percent to about 12.5 weight percent of the material. More specifically, the material contains about 10 weight percent of superabsorbent. Thus, the middle layer of the material could contain from about 15 g/m$^2$ to about 25 superabsorbent and from about 125 g/m$^2$ about 135 g/m$^2$ pulp and, more specifically about 20 g/m$^2$ superabsorbent and about 130 g/m$^2$ pulp. The middle layer containing pulp and superabsorbent can be laid down as a homogeneous blend or as a heterogeneous blend wherein the level of superabsorbent varies with proximity to the bottom layer.

In another embodiment, the second absorbent layer 48 is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 g/m$^2$ superabsorbent and from about 40 g/m$^2$ to about 65 g/m$^2$ pulp. When it is desired to keep absorbed fluid away from the cover layer 42 the amount of superabsorbent in the first and second middle layers is adjusted such that there is a higher level of superabsorbent in the second middle layer. The superabsorbent in the first and second middle layers can be the same or a different superabsorbent.

In one embodiment, the cellulosic fiber for use in the second absorbent layer 48 is wood pulp. There are certain characteristics of wood pulp that make it particularly suitable for use. Cellulose in most wood pulps has a crystalline form known as Cellulose I which can be converted to a form known as Cellulose II. In the second absorbent layer 48, wood pulp with a substantial portion of the cellulose as Cellulose II could be used. Similarly, pulps having an increased fiber curl value are advantageous. Finally, pulps having reduced levels of hemicellulose are preferred. Means for treating A pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus it could be advantageous that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60 degree C., but preferably at a temperature less than 50 degree C., and more preferably at a temperature between about 10 degree C. to 40 degree C. A preferred alkali metal salt solution is a sodium hydroxide solution newly made up or as a solution by-product in a pulp or paper mill operation, e.g., hemicaustic white liquor, oxidized white liquor and the like. Other alkali metal salts such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

For further details on the structure and the method of construction of the second absorbent layer 48 the reader is invited to refer to the U.S. Pat. No. 5,866,242 granted on Feb. 2, 1999 to Tan et al. The contents of this document are hereby incorporated by reference.

Main Body-Barrier Layer

Underlying the absorbent system 44 is a barrier layer 50 comprising liquid-impervious film material so as to prevent liquid that is entrapped in the absorbent system 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

The cover layer 42 and the barrier layer 50 are joined along their marginal portions so as to form an enclosure or flange seal that maintains the absorbent system 44 captive. The joint may be made by means of adhesives, heat-bonding, ultrasonic bonding, radio frequency sealing, mechanical crimping, and the like and combinations thereof. The peripheral seal line is shown in FIG. 1 by the reference numeral 52.

Flaps

The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent system 44. Alternatively, the flaps may include absorbent material between the cover layer and the barrier layer extensions. Such absorbent material may be an extension of the first absorbent layer 46, the second absorbent layer 48 or both. The flaps are optional and may have any other suitable shape than the one shown. Other fasteners may be provided, for example, adhesive fasteners placed on the barrier layer, as described below.

Adhesive System

Figure 3:
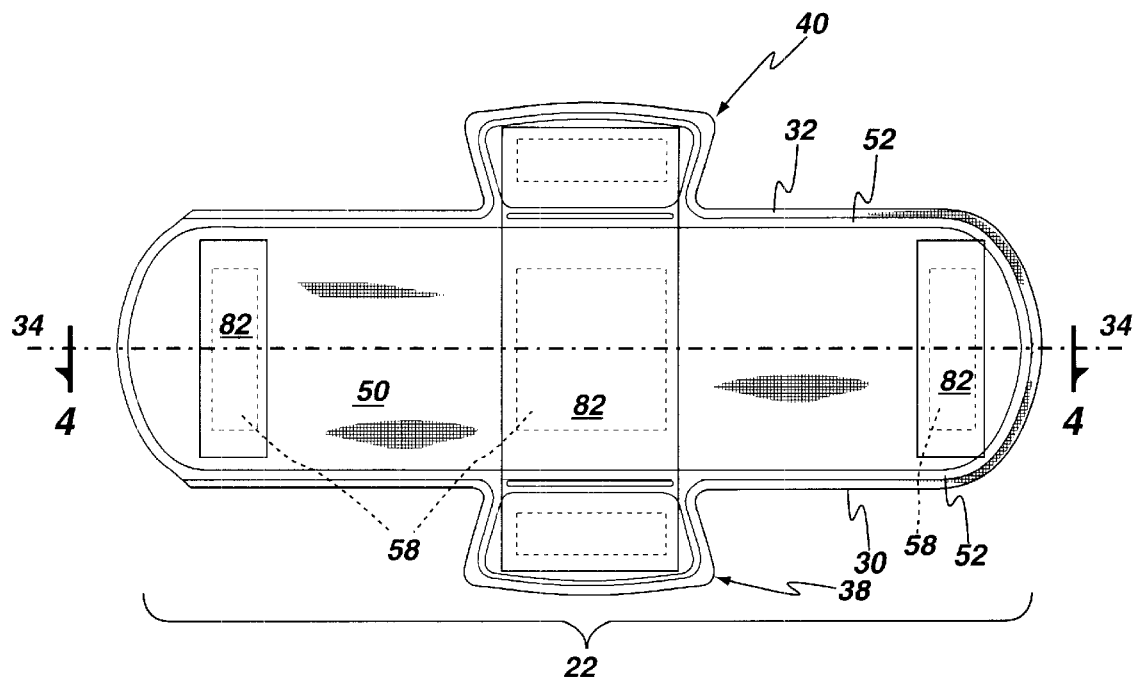
FIG. 3 is a bottom plan view of the sanitary napkin shown in FIG. 1.

Referring to FIGS. 2 and 3, in order to enhance the stability of the sanitary napkin, the garment facing surface of the barrier layer is provided with positioning adhesive material 58, typically hot-melt adhesive material capable of establishing a temporary bond with the undergarment material. A suitable material is the composition designated HL-1491 XZP commercially available from H. B. Fuller Canada, Toronto, Ontario, Canada. The positioning adhesive 58 may be applied to the garment-facing surface of the barrier layer 50 in various patterns, including complete adhesive coverage, parallel longitudinal lines, a line of adhesive following the perimeter of the structure, transverse lines of adhesive or the like.

Standard release paper 82 (shown only in FIG. 3) covers the positioning adhesive 58 before the napkin is used to prevent the unwanted adherence of the napkin to itself or foreign objects. The release paper is of conventional construction (e.g. silicone coated wet-laid Kraft wood pulp) and suitable papers are available from Tekkote Corporation (Leonia, N.J., USA), and bear the designation FRASER 30#/61629.

Channel Formations

In a preferred embodiment, the sanitary napkin is provided with at least one and preferably more than one channel formation arranged to direct liquid along the channel (or channels) for subsequent absorption into the first absorbent layer. The inventors have found that the provision of one or more channel(s) contributes to reducing the penetration time. Preferably, the napkin has a plurality of elongate channels formed therein, which are spaced apart from each other and configured to channel liquid across the body-facing surface of the napkin or near body facing surface thereof away from the region of initial deposition.

The provision of one or more channels adjacent the cover layer enables liquid to be transported rapidly over the napkin so that different regions of the first absorbent layer act together to absorb the liquid over a greater surface area. This helps to ensure that liquid is presented to a larger portion of the surface area of the second absorbent layer at the earliest opportunity.

The napkin may be provided with a single channel or multiple channels, for example running along or parallel to the longitudinal axis along the length of the napkin, obliquely of the longitudinal axis, for example from one side of the napkin to the other or substantially perpendicular to the longitudinal axis. The channel(s) may have any shape which may be selected according to the particular application, for example the channel(s) may be linear, arcuate or have a serpentine configuration or a mixture of these as well as other shapes, including spiral and zig-zag patterns.

In one embodiment, the napkin has a plurality of discrete channel formations which are spaced apart and intersect one another. An example of such an embodiment is shown in FIG. 1. Referring to FIG. 1, the napkin 20 is provided with a plurality of arcuate channels 10 which extend generally obliquely of the longitudinal centre line 34 from one side portion 12 to the opposite side portion 14. This design efficiently conducts liquid simultaneously along the length and across the width of the napkin. The channel formation(s) may be formed in the cover layer and/or in the first absorbent layer. The channels may be formed advantageously by applying localised pressure to the material as for example is used in embossing. The applied pressure results in densifying the material which defines the floor of the channel, extending the distance over which the liquid can travel before absorption. The second absorbent layer is preferably relatively thick in comparison with the other layers of the napkin which enables relatively deep channels to be formed. Advantageously, portions of the transfer layer laterally adjacent to the channel remain relatively thick and retain their original, relatively open pore structure allowing liquid to be efficiently drawn from the channel. Advantageously, the transfer layer comprises thermoplastic fibres. The provision of thermoplastic fibres assists in the formation of a stable and permanent channel when the thermoplastic fibres are subjected to heat. When heat is applied, the thermoplastic fibres tend to fuse together to form a more rigid structure so that the original form of the channels is maintained during use and overtime. Conveniently, the application of heat may be incorporated with the embossing process.

Method of Manufacture

The above-described embodiment of the sanitary napkin 20 is fabricated in a conventional manner in accordance with conventional techniques. Specifically, a laminate structure, sometimes referred to in the art as a web, is created. This laminate structure comprises an expanse of the materials from which the napkin will be created. The laminate structure comprises the following layers of material in a top-to-bottom order: an expanse of cover layer material; an expanse of first absorbent layer material; an expanse of second absorbent layer material (manufactured as described above); and finally an expanse of barrier layer. Some of the materials are necessarily not continuous within the laminate structure, and where such is the case, they are positioned precisely, one with respect to another, in the relationship they will occupy in the final products. The cover layer material and the barrier layer material are then bonded together by applying pressure in the appropriate positions, and what will become the peripheral seal is created. (The seal may also be made by means of heat-bonding, ultrasonic bonding, radio frequency sealing, mechanical crimping, and the like and combinations thereof.) The sealed structure is then severed by conventional means (i.e. die-cutting, fluid-jet cutting, or by laser) from the web to create a discrete article.

As mentioned above, one or more channels may be formed adjacent the body facing surface of the napkin, and the channel(s) may be formed for example by embossing. The channel(s) may be formed by other techniques, including cutting, excavating, etching, molding and cauterizing, as well as other methods known to those skilled in the art. If embossing is used, the method may involve passing the sanitary napkin between a pair of rollers, in which one of the rollers includes projections configured to the desired embossing pattern. The projections compress and densify the material locally and may be applied to the cover layer, the absorbent system (particularly, the first absorbent layer) or a combination of the two. The degree of pressure applied during the embossing operation depends upon the type of material and its physical integrity. Finding the optimal process conditions in accordance with the specific application is within the scope of a person skilled in the art. In general, the embossing pressure should be selected to sufficiently densify the material locally to form the channels but not too high so as to sever the material. As mentioned above, the material may also be heated and this may be done conveniently by heating the embossing rollers. Ultrasonic embossing may also be used for forming the channel(s).

Advantageously, embossing helps to hold the various layers of the sanitary napkin together and reduces the likelihood of the cover layer or the barrier layer separating from the adjacent layers or coming loose when the sanitary napkin is bent. Preferably, the napkin is embossed at regular intervals over the majority and preferably the entirety of the its surface.

The positioning adhesive material is then applied to the barrier layer in the appropriate positions, and release paper is applied to cover the positioning adhesive. Alternatively, the positioning adhesive, or the positioning adhesive and the release paper may be applied to the web before the individual articles are severed therefrom.

Procedure for Measuring Thickness of the Sanitary Napkin

As indicated earlier, the sanitary napkin 20 has a thickness of about 5 mm or less. The apparatus required to measure the thickness of the sanitary napkin is a footed dial (thickness) gauge with stand, available from Ames, with a 2" diameter foot and a readout accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are not considered when taking the thickness reading of the sample.

The foot of the gauge is raised and the sample placed on the anvil such that the foot of the gauge is approximately centred on the sample (or in the location of interest on the sample of interest). When lowering the foot, care is taken to avoid the foot dropping on to the sample or undue force being applied. After the foot is lowered, the sample should be allowed to stabilise for approximately 5 seconds, at which time the thickness reading is taken.

Liquid Penetration Test Procedure

The following test procedure is used to measure and define the penetration time of a sanitary absorbent napkin. The "penetration time" is a parameter related to the time which elapses between the moment when a 7 ml fluid first touches the sample (the fluid is applied with the apparatus described below) and the moment when the cover layer first appears through the top surface of the fluid. The time is measured to the nearest 0.1 seconds. This test is performed on five samples and an average value of the five samples is reported as the "Penetration time".

Figure 7:
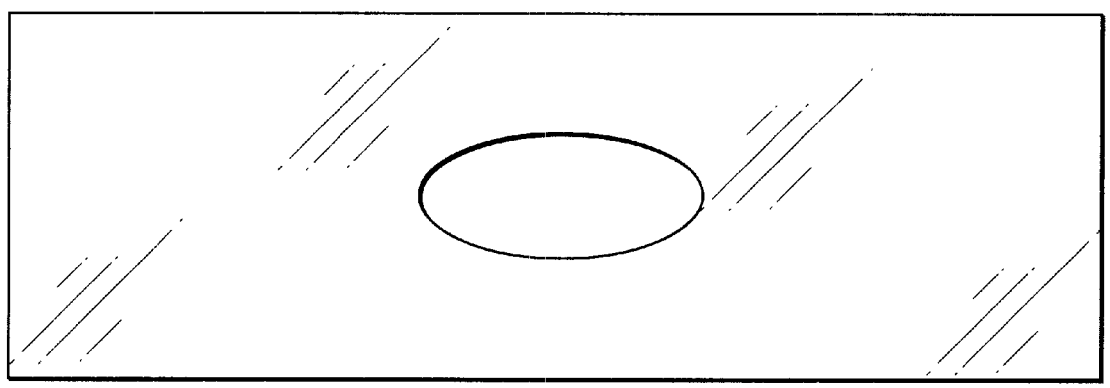
FIG. 7 shows a top view of a test plate used in measuring the penetration time.

The apparatus required for the test includes a stop watch with an accuracy to 0.1 sec, a graduated glass cylinder of 10 ml capacity and having an internal diameter of approximately 12 mm, a quantity of synthetic menstrual fluid, and a fluid penetration test orifice plate, as shown in FIG. 7. Referring to FIG. 7, the test plate is rectangular and made from Lexan and is 25.4 cm (10.0 inches) long by 7.6 cm (3.0 inches) wide by 1.27 cm (0.5 inches) thick. A concentric, elliptical orifice is formed through the plate having a major axis of length 3.8 cm and being parallel to the length of the plate and a minor axis of width 1.9 cm and being parallel to the width of the plate.

The apparatus further includes a resilient cushion for supporting the sanitary napkin during the penetration time test and which acts to improve the contact between the plate and cover layer. The cushion comprises a fusible fibre non-woven fabric (made with Enka fibres for example) of low density (0.03 to 0.5 g/cm$^3$) measured at 0.24 kPa (0.35 psi). The non-woven fabric is cut into rectangular sheets of dimensions 32×14 ×0.3 centimetres and the sheets are stacked until the stack reaches a free height of about 5 cm. The stack is then wrapped with one layer of 0.1 mm (0.004 inch) thick polyurethane elastomeric film such as BF Goodrich's Tuftane. The film wrap is sealed on the back with double-face clear tape to form a resilient cushion. This resilient cushion should respond to a load formation such as when using the Fraser Compressometer No. 255 equipped with the 12.7 cm (5 inch) diameter foot, the thickness of the cushion varying in the following way:

| Applied Pressure | Thickness (after being wrapped with film) |
| --- | --- |
| 0 pressure | 42.0 mm |
| 0.069 kPa (0.70 g/cm2; 0.01 psi) | 38.5 mm |
| 0.207 kPa (2.1 g/cm2; 0.03 psi) | 31.0 mm |
| 0.345 kPa (3.52 g/cm2; 0.05 psi) | 27.0 mm |
| 0.483 kPa (4.9 g/cm2; 0.07 psi) | 24.0 mm |

Sample Preparation

The sanitary absorbent napkin (with any packaging removed), the test fluid, the orifice plate and the graduated cylinders are conditioned at a temperature 21±☐ C. and 50±2% relative humidity (RH) for a minimum of 8 hours prior to testing. If the napkin is folded, the creases are removed as far possible by flattening and if the napkin is curved, the side gathers are cut through several times so that the sample can be flattened.

Procedure

The preconditioned sanitary napkin is placed on the resilient cushion on a level surface, without removing the release paper and with the cover layer facing upwards.

The cleaned orifice plate is placed on the sample, with the orifice centred on the napkin's surface so that the major axis of the elliptical orifice is coincident with the longitudinal axis of the napkin. If the napkin has at least one channel, the plate should be positioned so that at least one channel lies within the orifice or adjacent the edge of the orifice The graduated cylinder is then filled with 7 ml of synthetic menstrual test fluid. Suitable synthetic menstrual fluid has a viscosity of 30 centipoise (cps).

Holding the spout of the graduated cylinder approximately 1 to 3 inches above the orifice plate, the test fluid is poured into the orifice and the stop watch is started when the fluid first touches the sample. The stop watch is stopped when the cover layer first appears through the top surface of the fluid, regardless of where the cover layer becomes visible within the orifice. The fluid should be poured into the orifice in such a manner that the orifice is kept as full as possible without overflowing onto the face of the plate.

When conducting the above method, it is important that the tests are performed at a temperature of 21±1° C. and 50±2% relative humidity. It is also important that the samples, all components of the apparatus and the test fluid are conditioned for a minimum of eight hours at the conditions specified above prior to testing. The orifice plate should be thoroughly cleaned between test samples. Also, the test fluid container should not be left uncovered between testing of each sample as the evaporative effects will alter the fluid. It is also important that the correct end point is used when timing fluid penetration. If any of the above conditions are not met, the test results can be adversely affected.

The sanitary napkin embodying the present invention has excellent absorption characteristics and in particular, the unique combination of the properties of the transfer layer and absorbent core significantly reduce the time taken for the napkin to accept liquid, while at the same time allowing the napkin to remain thin with a relatively high absorption capacity. The napkin reduces the penetration time significantly in comparison with known napkins of similar thickness and advantageously virtually eliminates the risk of leakage of liquid from the edge of the transfer layer.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A sanitary napkin adapted to be worn in the crotch portion of an undergarment comprising:

a first liquid-permeable sheet of material, a second liquid-permeable sheet of material disposed adjacent the first sheet, an absorbent member for absorbing liquid and disposed adjacent the second sheet, said second sheet being arranged to receive liquid deposited on said first sheet and to transfer the liquid to said absorbent member, wherein said napkin has a thickness of less than or equal to about 5 mm, when dry, and a penetration time of less than 15 seconds.

2. A sanitary napkin as claimed in claim 1, wherein said absorbent member includes superabsorbent material.

3. A sanitary napkin as claimed in claim 2, wherein said absorbent member includes a mixture of cellulosic fibers and superabsorbent material.

4. A sanitary napkin as claimed in claim 3, wherein said absorbent member comprises an absorbent material having a basis weight of from about 100 g/m$^2$ to about 700 g/m$^2$ which has been air-laid as a bottom layer of pulp, a middle layer of pulp and superabsorbent polymer disposed in amongst the pulp, and a top layer containing at least some pulp.

5. A sanitary napkin as claimed in claim 4, wherein said absorbent material has a density more than about 0.25 g/cc.

6. A sanitary napkin as claimed in claim 4, wherein said absorbent material includes from about 5 weight percent to about 60 weight percent superabsorbent polymer.

7. A sanitary napkin as claimed in claim 4, wherein said absorbent material has a basis weight in the range from about 150 g/m² to about 350 g/m².

8. A sanitary napkin as claimed in claim 7, wherein said absorbent material has a basis weight in the range from about 200 g/m² to about 300 g/m².

9. A sanitary napkin as claimed in claim 7, wherein said absorbent material has a basis weight of about 250 g/m².

10. A sanitary napkin as claimed in claim 7, wherein said absorbent material has a density in the range from about 0.3 g/cc to about 0.5 g/cc.

11. A sanitary napkin as claimed in claim 10, wherein said absorbent material has a density in the range from about 0.3 g/cc to about 0.45 g/cc.

12. A sanitary napkin as claimed in claim 4, wherein the middle it layer comprises a first middle layer adjacent the bottom layer and a second middle layer adjacent the top layer.

13. A sanitary napkin as claimed in claim 6, wherein said absorbent material includes from about 20 weight percent to about 55 weight percent superabsorbent polymer.

14. A sanitary napkin as claimed in claim 13, wherein said absorbent material includes from about 30 weight percent to about 45 weight percent superabsorbent polymer.

15. A sanitary napkin as claimed in claim 14, wherein said absorbent material includes about 40 weight percent superabsorbent polymer.

16. A sanitary napkin as claimed in claim 15, wherein said second sheet is air laid over said top layer of said absorbent member.

17. A sanitary napkin claimed in claim 1, further comprising a further sheet of material disposed adjacent said absorbent member and being substantially impervious to liquid.

18. A sanitary napkin as claimed in claim 1, wherein the thickness of the sanitary napkin is less than about 3 mm.

19. A sanitary napkin as claimed in claim 18, wherein the thickness of the sanitary napkin is about 2.8 mm.

20. A sanitary napkin as claimed in claim 1, wherein said second sheet of material comprises thermoplastic fibers.

21. A sanitary napkin as claimed in claim 1, further comprising a fastener for fastening said napkin to a garment of the wearer.

22. A sanitary napkin as claimed in claim 21, wherein said fastener comprises an adhesive fastener.

23. A sanitary napkin as claimed in claim 22, further comprising a flap carrying said adhesive fastener.

24. A sanitary napkin as claimed in claim 1, having an elongate channel formation arranged to direct liquid there along for subsequent absorption into said second sheet.

25. A sanitary napkin as claimed in claim 24, further comprising a plurality of said elongate channel formations spaced apart from each other.

26. A sanitary napkin as claimed in claim 25, wherein said elongate channel formations intersect each other.

27. A sanitary napkin as claimed in claim 24, wherein said elongate channel formation is arcuate in a plane parallel to said second sheet.

28. A sanitary napkin as claimed in claim 24, wherein said elongate channel formation is formed in at least one of said first and second sheet.

29. A sanitary napkin as claimed in claim 24, wherein said elongate channel formation is formed by applying pressure to at least one of said first and second sheets.

30. A sanitary napkin as claimed in claim 29, wherein said elongate channel formation is formed by applying heat to at least one of said first and second sheets.

31. A sanitary napkin as claimed in claim 24, wherein the material adjacent the floor of said channel formation has a higher density than the material on at least one side of said channel formation.

32. A sanitary napkin as claimed in claim 24, wherein said napkin has a longitudinal axis and two opposite longitudinal side areas, and said channel extends obliquely off said longitudinal axis from one said longitudinal side area to the opposite longitudinal side area, crossing said longitudinal axis.

33. A sanitary napkin as claimed in claim 1, wherein, at the interface between said first and second sheets, an elongate region is recessed in said second sheet, said elongate region having a higher density than a second region adjacent thereto.

34. A sanitary napkin as claimed in claim 32, further comprising a plurality of said elongate regions.

35. A sanitary napkin as claimed in claim 1, wherein said second sheet comprises a material having a density of between about 0.04 and 0.05 g/cc.

36. A sanitary napkin as claimed in claim 1, wherein said second sheet comprises a material having a basis weight in the range from about 80 g/m² to about 110 g/m².

37. A sanitary napkin as claimed in claim 1, wherein said second sheet has a thickness in the range from about 2 mm to about 3 mm.

* * * * *